(12) United States Patent
Suzuki et al.

(10) Patent No.: US 7,091,381 B2
(45) Date of Patent: Aug. 15, 2006

(54) PROCESS FOR PREPARATION OF CYCLOHEXANONE OXIME

(75) Inventors: Ken Suzuki, Kurashiki (JP); Hajime Nagahara, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 10/482,835

(22) PCT Filed: Jul. 25, 2002

(86) PCT No.: PCT/JP02/07546

§ 371 (c)(1),
(2), (4) Date: Jan. 6, 2004

(87) PCT Pub. No.: WO03/010133

PCT Pub. Date: Feb. 6, 2003

(65) Prior Publication Data

US 2004/0176592 A1    Sep. 9, 2004

(30) Foreign Application Priority Data

Jul. 25, 2001    (JP)    ............................ 2001-224029

(51) Int. Cl.
*C07C 249/00*    (2006.01)

(52) U.S. Cl. .................................................... 564/267

(58) Field of Classification Search ................. 564/267
See application file for complete search history.

(56) References Cited

U.S. PATENT DOCUMENTS

| 3,346,636 | A | * | 10/1967 | Barker | ........................ 564/446 |
| 5,026,911 | A | * | 6/1991 | Venturello et al. | ........... 564/253 |
| 5,312,987 | A | * | 5/1994 | Mantegazza et al. | ........ 564/267 |
| 6,245,907 | B1 | * | 6/2001 | Suh et al. | .................... 540/534 |

FOREIGN PATENT DOCUMENTS

| EP | 395046 | * 10/1990 |
| JP | 51-41627 B1 | 11/1976 |

* cited by examiner

*Primary Examiner*—Johann Richter
*Assistant Examiner*—Chukwuma Nwaonicha
(74) *Attorney, Agent, or Firm*—Birch, Stewart, Kolasch & Birch, LLP

(57) ABSTRACT

A method for producing cyclohexanone oxime, which comprises the steps of (1) subjecting to an amination reaction a starting material selected from the group consisting of cyclohexanol, cyclohexanone and a mixture thereof, thereby obtaining cyclohexylamine, and (2) subjecting the obtained cyclohexylamine to a partial oxidation reaction, thereby obtaining cyclohexanone oxime, wherein a by-product ($\alpha$) formed in the step (1) and/or a by-product ($\beta$) formed in the step (2) are/is recycled to a reaction system of the amination reaction in the step (1).

9 Claims, No Drawings

PROCESS FOR PREPARATION OF CYCLOHEXANONE OXIME

BACKGROUND OF THE INVENTION

1. Field of the Invention

The present invention relates to a method for producing cyclohexanone oxime. More particularly, the present invention is concerned with a method for producing cyclohexanone oxime, which comprises the steps of: (1) subjecting to an amination reaction a starting material selected from the group consisting of cyclo-hexanol, cyclohexanone and a mixture thereof, thereby obtaining cyclohexylamine, and (2) subjecting the obtained cyclohexylamine to a partial oxidation reaction, thereby obtaining cyclohexanone oxime, wherein a by-product ($\alpha$) formed in the step (1) and/or a by-product ($\beta$) formed in the step (2) are/is recycled to a reaction system of the amination reaction in the step (1). By the method of the present invention, cyclohexanone oxime, which is a useful compound as an intermediate of $\epsilon$-caprolactam ($\epsilon$-caprolactam is well-known as a raw material for producing nylon 6 or the like), can be produced with high selectivity, and with other various great advantages in that production of cyclohexanone oxime can be performed, using a simple apparatus, by a simple operation with less consumption of hydrogen, and with no need for use of a difficult reagent, such as a hydroxylamine salt. In the conventional methods for producing cyclohexanone oxime, it is usually required to use a hydroxylamine salt; however, a hydroxylamine salt can be obtained only by a method involving complicated steps, leading to disadvantages.

Further, the method of the present invention is free from problems accompanying the prior art, such as generation of a by-product which is difficult to separate and which adversely affects the quality of $\epsilon$-caprolactam produced from cyclohexanone oxime, and/or generation of a by-product (e.g., ammonium sulfate) which is of little commercial value. Furthermore, most of the by-products produced in the method of the present invention are recyclable, and with respect to the other by-products, which are not recyclable, most of them are useful compounds, such as cyclohexane and the like, so that generation of wastes can be suppressed to an extremely low level. Thus, the method of the present invention is commercially very advantageous.

2. Prior Art

Conventionally, various methods for producing cyclohexanone oxime have been known. Of such methods, most widely practiced on a commercial scale is a method which consists in producing cyclohexanone from benzene as a starting material by a multi-stage process, and reacting the produced cyclohexanone with a hydroxylamine salt which has been separately produced from ammonia, to thereby obtain cyclohexanone oxime. More specifically, the most widely practiced method involves the following three steps:

(I) producing cyclohexanone from benzene as a starting material, (II) providing a hydroxylamine salt which has been separately produced from ammonia, and (III) reacting the cyclohexanone with the hydroxylamine salt to thereby obtain cyclohexanone oxime.

With respect to a representative process for realizing the step (I) of producing cyclohexanone, reference can be made to "Kagakukougaku (Chemical Engineering)", Vol. 55 (1991), No. 5, page 382, published by The Society of Chemical Engineers, Japan, and "Shokubai (Catalysts and Catalysis)", Vol. 33 (1991), No. 5, page 341, published by The Catalysis Society of Japan. The most representative process for the step (I) involves oxidation of cyclohexane with air. Another process, which involves hydrogenation of phenol, is also some-times practiced. With respect to the above-mentioned most representative process (i.e., the process involving oxidation of cyclohexane with air), an explanation is made below. This process comprises completely hydrogenating benzene to obtain cyclohexane, subjecting the obtained cyclohexane to oxidation with air to obtain a mixture of cyclohexanol and cyclohexanone, separating the mixture into cyclohexanol and cyclohexanone by distillation, and dehydrogenating the separated cyclohexanol to obtain cyclohexanone.

However, this process has the following disadvantages. First, the process requires a number of steps. Further, in the step of oxidation of cyclohexane with air, for improving the selectivity, it is required to suppress the conversion of cyclohexane to about 3 to 10%, so that the productivity is inevitably lowered. Also, a large amount of energy is needed for recycling the cyclohexane which remains unreacted. Furthermore, the improved selectivity is still unsatisfactorily at a level of from about 73 to 83%. In this process, as by-products, carboxylic acids, alcohols, aldehydes, ketones, ethers, esters, hydrocarbons and the like are generated. In general, these by-products are separated from the desired products (i.e., cyclohexanol and cyclohexanone) and discarded. Of the above-mentioned by-products, water-soluble carboxylic acids, water-soluble lower alcohols and the like can be removed by extraction with water. With respect to the carboxylic acids and esters, which are not water-soluble, such by-products can be removed by saponification with an aqueous alkali solution. Further, most of the other by-products can be removed in the subsequent distillation step. However, with respect to the by-products (such as butyl cyclohexyl ether, n-pentylcyclohexane, cyclohexyl acetate and hexahydrobenzaldehyde) having a boiling point which is very close to that of cyclohexanone or cyclohexanol, it is difficult to remove such by-products, and the presence of these by-products causes a lowering of the quality of the desired compound, i.e., $\epsilon$-caprolactam. Methods for removing the by-products are disclosed in patent documents, such as Examined Japanese Patent Application Publication No. Sho 60-39656 (corresponding to U.S. Pat. No. 4,661,430), Unexamined Japanese Patent Application Laid-Open Specification No. Hei 5-271143 and Unexamined Japanese Patent Application Laid-Open Specification No. Hei 5-301858. However, each of the methods disclosed in these patent documents needs a number of cumbersome separation steps and, hence, is not advantageous.

As another method for oxidation of cyclohexane with air, a method is known in which the oxidation is performed in the presence of boric acid. By this method, the conversion and the selectivity are, respectively, improved to a level of from about 12 to 15% and a level of about 90%. However, this method is disadvantageous in that not only is it difficult to handle cyclohexane and a boric acid slurry, but also recycling of these difficult cyclohexane and boric acid slurry is necessary, and the operations therefor are cumbersome.

Further, in the above-mentioned step of dehydrogenation of cyclohexanol, the conversion of cyclohexanol is inevitably limited to at most 70 to 90% due to the equilibrium of the reaction. Also, the boiling point of cyclohexanol as a raw material is very close to that of cyclohexanone obtained as a product, so that a large amount of energy is needed for separating cyclohexanol from cyclohexanone.

With respect to the above-mentioned process for the step (I), which involves hydrogenation of phenol, an explanation is made below. The process involving hydrogenation of phenol has been known since a long time ago. This process comprises producing phenol from benzene, subjecting the produced phenol to hydrogenation at the benzene nucleus in the presence of nickel, palladium or the like as a catalyst to thereby obtain cyclohexanol or cyclohexanone. This process also poses problems. For example, when the production of phenol from benzene is conducted by the cumene process, which is a representative process for production of phenol from benzene, the following disadvantages are caused. The cumene process involves a number of reaction steps. Further, in the cumene process, commercially valuable acetone is coproduced with phenol. Therefore, the cumene process is generally performed using a complicated and expensive apparatus which are needed for separating acetone and phenol from each other, and the demand for and the price of the coproduced acetone influence the production cost of phenol, thereby rendering it difficult to stably supply phenol.

With respect to the above-mentioned step (II) of producing a hydroxylamine salt from ammonia, an explanation is made below. As a representative process for the step (II), there can be mentioned the Raschig process, which is a classical process (see "Kougyou Yuukikagaku (Industrial Organic Chemistry)", fourth edition, page 287 (1996), translated under supervision of Teruaki Mukaiyama, TOKYO KAGAKU DOZIN CO., LTD., Japan). This process involves four steps. Specifically, the process involves producing ammonium carbonate from ammonia, carbon dioxide and water, synthesizing ammonium nitrite from the produced ammonium carbonate and a mixture of NO and $NO_2$ (wherein the mixture is obtained by oxidation of ammonia with air), reducing the synthesized ammonium nitrate using $SO_2$ to obtain a disulfonate, and hydrolyzing the obtained disulfonate to obtain a sulfuric acid salt of hydroxylamine. This process poses the following problems. The process involves complicated steps. Further, ammonium sulfate, which is of little commercial value, is generated in an amount equimolar to the sulfuric acid salt of hydroxylamine. That is, when the amount of ammonium sulfate by-produced in the oximation is also taken into consideration, the amount of ammonium sulfate by-produced is two moles, relative to one mole of the finally produced cyclohexanone oxime.

Further, with respect to the hydroxylamine sulfate-oxime process (HSO process) and the hydroxylamine phosphate-oxime process (HPO process), each of these processes consists in producing a hydroxylamine salt, and producing cyclohexanone oxime using the produced hydroxylamine salt. These processes also pose various problems, as described below in connection with the above-mentioned step (III).

As a representative process for the step (III), there can be mentioned a process involving oximation of cyclohexanone by the use of a sulfuric acid salt of hydroxylamine (see "Kougyou Yuukikagaku (Industrial Organic Chemistry)", fourth edition, page 285 (1996), translated under supervision of Teruaki Mukaiyama, TOKYO KAGAKU DOZIN CO., LTD., Japan). The reaction for the oximation is an equilibrium reaction, so that, for advancing the reaction, it is necessary to maintain the pH value at about 7 by adding a certain amount of ammonia to the reaction system. However, when ammonia is added, ammonium sulfate, which is of little commercial value, is inevitably by-produced in an amount equimolar to cyclohexanone oxime.

In connection with the above-mentioned steps (II) and (III), the above-mentioned HSO and HPO processes are explained below. The HSO process involves oxidizing ammonia in the presence of a platinum-containing catalyst to obtain NO, subjecting the obtained NO to reduction with hydrogen in the presence of a platinum-containing catalyst using an ammonium hydrogensulfate/ammonium sulfate buffer solution to produce hydroxylammonium sulfate, and reacting the produced hydroxylammonium sulfate with cyclohexanone (see, for example, U.S. Pat. Nos. 3,941,838 and 4,031,139). The HPO process involves oxidizing ammonia to obtain nitric acid ion, subjecting the obtained nitric acid ion to reduction with hydrogen in the presence of palladium as a catalyst using a phosphoric acid/monoammonium phosphate buffer solution to produce a phosphoric acid salt of hydroxylamine, and reacting the produced phosphoric acid salt of hydroxylamine with cyclohexanone (see, for example, U.S. Pat. Nos. 3,948,988 and 3,940,442). Each of the above-mentioned HSO and HPO processes is advantageous in that the pH value is maintained at a certain level because the buffer solution is allowed to circulate between the cyclohexanone oxime production system and the hydroxylamine salt production system, so that by-production of ammonium sulfate can be prevented. However, the process has the following disadvantages. The process involves a number of reaction steps. Further, high purity raw materials are needed. Furthermore, the step of recovering the catalyst and the step of recycling the buffer solution are complicated. Also, in the whole process, the ammonia-based selectivity for the hydroxylamine salt is as low as about 60%.

Further, the method involving the above-mentioned steps (I) to (III) poses a problem that, for complete hydrogenation of benzene, production of a hydroxylamine salt, and the like, a large amount of hydrogen is needed.

It has been attempted to improve the above-mentioned method involving the steps (I) to (III). For example, with respect to the process for producing cyclohexanone, a process has been proposed which involves subjecting benzene to partial hydrogenation to obtain cyclohexene, hydrating the obtained cyclohexene to obtain cyclohexanol, and subjecting the obtained cyclohexanol to dehydrogenation to obtain cyclohexanone (see Unexamined Japanese Patent Application Laid-Open Specification No. Sho 56-43227 (corresponding to EP 23379)). This process is advantageous not only in that the amount of hydrogen consumed is small as compared to the case of the above-mentioned method involving subjecting cyclohexane to oxidation with air, but also in that it is possible to achieve a carbon-based yield of substantially 100%, wherein the "carbon-based yield" means the total yield of cyclohexanone produced and cyclohexane by-produced in the partial hydrogenation of benzene. However, the process poses various problems. For example, not only does the reaction apparatus used in the step of dehydrogenation of cyclohexanol inevitably become large, but also the necessary energy cost is high, as compared to the case of the above-mentioned process for subjecting cyclohexane to oxidation with air.

As another improved method, there is known a method involving reacting cyclohexanone with ammonia in the presence of hydrogen peroxide to obtain cyclohexanone oxime (see U.S. Pat. No. 4,745,221). This method is advantageous not only in that a difficult reagent (e.g., a hydroxylamine salt) which can be obtained only by a method involving complicated steps is not needed, but also in that ammonium sulfate is not by-produced. However, the method has a problem that hydrogen peroxide, which is expensive, is needed.

On the other hand, methods involving no step of producing cyclohexanone have also been practiced on a commercial scale. As an example of such methods, there can be mentioned a method which involves subjecting benzene to complete hydrogenation to obtain cyclohexane, and reacting the obtained cyclohexane with nitrosyl chloride to obtain a hydrochloric acid salt of cyclohexanone oxime, wherein the nitrosyl chloride is produced by reacting a mixture of NO and $NO_2$ (which mixture is obtained by oxidation of ammonia with air) with sulfuric acid, and then with hydrochloric acid (see "Yuukigousei Kagaku Kyoukaishi (Journal of Synthetic Organic Chemistry, Japan), Vol. 21 (1963), pages 160–163, published by The Society of Synthetic Organic Chemistry, Japan). This method is advantageous in that the number of reaction steps in the method is small as compared to that in the method involving a step of producing cyclohexanone as an intermediate material. However, the method has the following disadvantages. Light is needed for the oximation, so that not only is a large amount of power needed for the oximation, but also maintenance of a mercury lamp or the like used for irradiation of light is cumbersome.

As another method involving no step of producing cyclohexanone, there can be mentioned a method which involves subjecting benzene to complete hydrogenation to obtain cyclohexane, reacting the obtained cyclohexane with nitric acid (which is obtained by oxidation of ammonia) to obtain nitrocyclohexane, and subjecting the obtained nitrocyclohexane to partial hydrogenation to obtain cyclohexanone oxime (see, for example, U.S. Pat. Nos. 3,255,261 and 2,967,200). This method has various problems. For example, the oxidation reaction using nitric acid is required to be performed at a temperature as high as about 150 to 200° C. under a pressure as high as about 3 to 4 MPa, and the apparatus used in the method are greatly corroded. In addition, this method has a danger of explosion. Further, the selectivity for nitrocyclohexane is not satisfactory. Specifically, each of the cyclohexane-based selectivity and the nitric acid-based selectivity is only about 80%. The conversion of cyclohexane is also as low as 15 to 25%. Thus, the productivity is low, and a large amount of energy is needed for recycling the cyclohexane which remains unreacted. Moreover, in the step of producing cyclohexanone oxime by subjecting nitrocyclohexane to partial hydrogenation, the selectivity for cyclohexanone oxime is unsatisfactorily only about 80%.

As apparent from the above, the conventional methods for producing cylohexanone oxime have a serious problem in that the methods inevitably need complicated steps. Therefore, it has been desired to develop a simple and efficient method for producing cyclohexanone oxime, which can be practiced on a commercial scale.

SUMMARY OF THE INVENTION

In this situation, the present inventors have made extensive and intensive studies with a view toward solving the above-mentioned problems accompanying the prior art. As a result, it has unexpectedly been found that the above-mentioned problems can be solved by a method for producing cyclohexanone oxime, which comprises the steps of: (1) subjecting to an amination reaction a starting material selected from the group consisting of cyclohexanol, cyclohexanone and a mixture thereof, thereby obtaining cyclohexylamine, and (2) subjecting the obtained cyclohexylamine to a partial oxidation reaction, thereby obtaining cyclohexanone oxime, wherein a by-product ($\alpha$) formed in the step (1) and/or a by-product ($\beta$) formed in the step (2) are/is recycled to a reaction system of the amination reaction in the step (1). That is, by the above-mentioned method, cyclohexanone oxime can be produced with high selectivity, and with other various great advantages in that production of cyclohexanone oxime can be performed, using a simple apparatus, by a simple operation with less consumption of hydrogen, and with no need for use of a difficult reagent, such as a hydroxylamine salt. In the conventional methods for producing cyclohexanone oxime, it is usually required to use a hydroxylamine salt; however, a hydroxylamine salt can be obtained only by a method involving complicated steps, leading to disadvantages. Further, the method is free from problems accompanying the prior art, such as generation of a by-product which is difficult to separate and which adversely affects the quality of $\epsilon$-caprolactam produced from cyclohexanone oxime, and/or generation of a by-product (e.g., ammonium sulfate) which is of little commercial value. Furthermore, most of the by-products generated in the method are recyclable, and with respect to the other by-products, which are not recyclable, most of them are useful compounds, such as cyclohexane and the like, so that generation of wastes can be suppressed to an extremely low level. Therefore, the method is commercially very advantageous. Based on these findings, the present invention has been completed.

Accordingly, it is a primary object of the present invention to provide a method for producing cyclohexanone oxime (which is a useful compound as an intermediate of $\epsilon$-caprolactam, wherein the $\epsilon$-caprolactam is useful as a raw material for producing nylon 6 or the like) with high selectivity. The method further has the following great advantages. Production of cyclohexanone oxime can be performed, using a simple apparatus, by a simple operation with less consumption of hydrogen, and with no need for use of a difficult reagent, such as a hydroxylamine salt. In the conventional methods for producing cyclohexanone oxime, it is usually required to use a hydroxylamine salt; however, a hydroxylamine salt can be obtained only by a method involving complicated steps, leading to disadvantages. Further, the objective method is free from problems accompanying the prior art, such as generation of a by-product which is difficult to separate and which adversely affects the quality of $\epsilon$-caprolactam produced from cyclohexanone oxime, and/or generation of a by-product (e.g., ammonium sulfate) which is of little commercial value. Furthermore, most of the by-products generated in the method are recyclable, and with respect to the other by-products, which are not recyclable, most of them are useful compounds, such as cyclohexane and the like, so that the generation of wastes can be suppressed to an extremely low level.

The foregoing and other objects, features and advantages of the present invention will be apparent from the following detailed description and appended claims.

DETAILED DESCRIPTION OF THE INVENTION

According to the present invention, there is provided a method for producing cyclohexanone oxime, which comprises the steps of:

(1) subjecting to an amination reaction a starting material selected from the group consisting of cyclohexanol, cyclohexanone and a mixture thereof, thereby obtaining cyclohexylamine, and (2) subjecting the obtained cyclohexylamine to a partial oxidation reaction, thereby obtaining cyclohexanone oxime, wherein at least one by-product selected from the group consisting of a by-product (α) formed in the step (1) and a by-product (α) formed in the step (2) is recycled to a reaction system of the amination reaction in the step (1).

For easy understanding of the present invention, the essential features and various preferred embodiments of the present invention are enumerated below.

1. A method for producing cyclohexanone oxime, which comprises the steps of:

(1) subjecting to an amination reaction a starting material selected from the group consisting of cyclohexanol, cyclohexanone and a mixture thereof, thereby obtaining cyclohexylamine, and (2) subjecting the obtained cyclohexylamine to a partial oxidation reaction, thereby obtaining cyclohexanone oxime, wherein at least one by-product selected from the group consisting of a by-product (α) formed in the step (1) and a by-product (β) formed in the step (2) is recycled to a reaction system of the amination reaction in the step (1).

2. The method according to item 1, wherein:

when cyclohexanol is used as the starting material in the step (1), the by-product (α) comprises at least one compound selected from the group consisting of cyclohexanone, N-(cyclohexylidene)-cyclohexylamine, dicyclohexylamine, cyclohexylaniline and aniline, when cyclohexanone is used as the starting material in the step (1), the by-product (α) comprises at least one compound selected from the group consisting of cyclohexanol, N-(cyclohexylidene)-cyclohexylamine, dicyclohexylamine, cyclohexylaniline and aniline, and when a mixture of cyclohexanol and cyclohexanone is used as the starting material in the step (1), the by-product (α) comprises at least one compound selected from the group consisting of cyclohexanol, cyclohexanone, N-(cyclohexylidene)cyclohexylamine, dicyclohexylamine, cyclohexylaniline and aniline; and wherein the by-product (β) comprises at least one compound selected from the group consisting of cyclohexanone, nitrocyclohexane, N-(cyclohexylidene)cyclohexylamine and dicyclohexylamine.

3. The method according to item 1, wherein the amination reaction in the step (1) is performed in the presence of an amination catalyst comprising at least one element selected from the group consisting of elements belonging to Groups 8, 9 and 10 of the Periodic Table, chromium, copper, silver, zinc and aluminum.

4. The method according to item 3, wherein the amination reaction in the step (1) is performed in the presence of molecular hydrogen.

5. The method according to item 1, wherein the partial oxidation reaction in the step (2) is performed in the presence of molecular oxygen as an oxidizing agent.

6. The method according to item 1, wherein the cyclohexanol is produced by a process comprising (i) subjecting benzene to partial hydrogenation to obtain a cyclohexene, and (ii) subjecting the obtained cyclohexene to hydration.

7. The method according to item 6, wherein the partial hydrogenation of benzene is performed in the presence of a hydrogenation catalyst comprising at least one element selected from the group consisting of elements belonging to Groups 8, 9 and 10 of the Periodic Table, and water.

8. The method according to item 6, wherein the partial hydrogenation of benzene is performed in a neutral or acidic liquid phase in the presence of (a) a hydrogenation catalyst which comprises metallic ruthenium having an average crystallite size of 200 Å or less and optionally a zinc compound, (b) water, and (c) at least one compound selected from the group consisting of an oxide of zirconium or hafnium, a water-soluble zinc compound and solid, basic zinc sulfate, wherein the hydrogenation catalyst is used in a non-supported form.

9. The method according to item 6, wherein the hydration of cyclohexene is performed in the presence of a zeolite as a hydration catalyst.

10. The method according to item 9, wherein the zeolite is selected from the group consisting of zeolites of ZSM-5 family.

11. The method according to item 1, wherein the cyclohexanone is produced by a process comprising (i) subjecting benzene to partial hydrogenation to obtain cyclohexene, (ii) subjecting the obtained cyclohexene to hydration to obtain cyclohexanol, and (iii) subjecting the obtained cyclohexanol to dehydrogenation.

12. The method according to item 11, wherein the partial hydrogenation of benzene is performed in the presence of a hydrogenation catalyst comprising at least one element selected from the group consisting of elements belonging to Groups 8, 9 and 10 of the Periodic Table, and water.

13. The method according to item 11, wherein the partial hydrogenation of benzene is performed in a neutral or acidic liquid phase in the presence of (a) a hydrogenation catalyst which comprises metallic ruthenium having an average crystallite size of 200 Å or less and optionally a zinc compound, (b) water, and (c) at least one compound selected from the group consisting of an oxide of zirconium or hafnium, a water-soluble zinc compound and solid, basic zinc sulfate, wherein the hydrogenation catalyst is used in a non-supported form.

14. The method according to item 11, wherein the hydration of cyclohexene is performed in the presence of a zeolite as a hydration catalyst.

15. The method according to item 14, wherein the zeolite is selected from the group consisting of zeolites of ZSM-5 family.

Hereinbelow, the present invention is described in detail.

In the step (1) of the method of the present invention, a starting material selected from the group consisting of cyclohexanol, cyclohexanone and a mixture thereof is subjected to an amination reaction, thereby obtaining cyclohexylamine. The amination reaction in the step (1) is performed in the presence of ammonia, preferably in the presence of ammonia and molecular hydrogen, using a catalyst. Specifically, the amination reaction can be performed by the conventional processes. Examples of conventional processes for amination of cyclohexanol include a process comprising reacting cyclohexanol with ammonia in a gaseous phase in the presence of molecular hydrogen, using copper oxide/zinc oxide as a catalyst (see "Kougyou Kagaku Zasshi (Journal of the Society of Chemical Industry)", Vol. 70 (1967), No. 9, page 1508, published by the Chemical Society of Japan); a process comprising reacting cyclohexanol with ammonia in a gaseous phase in the presence of molecular hydrogen, under atmospheric pressure using a reduced nickel-forming catalyst, wherein the catalyst is supported on diatomaceous earth (see Examined Japanese Patent Application Publication No. Sho 51-41627); a process comprising reacting cyclohexanol with ammonia in a liquid phase at high temperature in the presence of molecular hydrogen under high pressure using a catalyst comprised mainly of cobalt (see Examined Japanese Patent Application Publication No. Sho 51-32601; and a process comprising reacting an alicyclic alcohol (e.g., cyclohexanol) with ammonia in the presence of a ruthenium catalyst pretreated with hydrogen (see Unexamined Japanese Patent Application Laid-Open Specification No. Hei 5-148191). Examples of conventional processes for amination of cyclohexanone include a process comprising reacting cyclohexanone with ammonia in the presence of molecular hydrogen, using a catalyst, such as nickel, cobalt, platinum or palladium (see Chemical Abstract Vol. 15 (1921) page 1285); and a process comprising reacting cyclohexanone with ammonia in a liquid phase in the presence of molecular hydrogen, using a nickel catalyst (see "Kougyou Kagaku Zasshi (Journal of the Society of Chemical Industry)", Vol. 70 (1967), No. 8, page 1335, published by the Chemical Society of Japan). Further, examples of conventional processes for amination of a mixture of cyclohexanol and cyclohexanone include a process comprising reacting the cyclohexanol/cyclohexanone mixture with ammonia in a gaseous phase in the presence of molecular hydrogen, using a nickel oxide-chrome oxide catalyst (see French Patent No. 1,492,098); and a process comprising reacting the cyclohexanol/cyclohexanone mixture with ammonia in a gaseous phase in the presence of molecular hydrogen, using a catalyst composed of nickel and/or cobalt, and phosphoric acid or boric acid (see Examined Japanese Patent Application Publication No. Sho 41-7575).

As the amination catalyst for amination of cyclohexanol and/or cyclohexanone, there can be mentioned various metals, metal oxides, metal salts and organometal compounds. It is preferred that the amination catalyst comprises at least one metal selected from the group consisting of metals belonging to Groups 8, 9 and 10 of the Periodic Table (such as Fe, Co, Ni, Ru, Rh, Pd, Ir and Pt), Cr, Cu, Ag, Zn and Al. In the amination catalyst, each of the above-mentioned metals may be in the form of a metal oxide, and the catalyst may comprise a carrier having supported thereon the above-mentioned metal(s) or metal oxide(s). Examples of carriers include an activated carbon, $SiO_2$, $Al_2O_3$, $SiO_2/Al_2O_3$, $TiO_2$, $ZrO_2$, ZnO, barium sulfate, potassium carbonate, diatomaceous earth and a zeolite.

The amination reaction of cyclohexanol and/or cyclohexanone in the step (1) can be performed in a gaseous or liquid phase using a fixed-bed or slurry-bed reactor. The reaction can be performed in a continuous or batchwise manner. When the reaction is performed in a liquid phase, a solvent can be used. With respect to the solvent, there is no particular limitation. Examples of solvents include nitrites, such as acetonitrile and propionitrile; aliphatic hydrocarbons, such as n-hexane and cyclohexane; aromatic compounds, such as benzene and toluene; ethers, such as dioxane and diglyme; and water. When the amination reaction is performed in the presence of a solvent, the amount of cyclohexanol and/or cyclohexanone is generally from 1 to 30% by weight, preferably from 5 to 20% by weight, based on the total weight of cyclohexanol and/or cyclohexanone, and the solvent. The solvent can also be used when the amination reaction is performed in a gaseous phase. In this case, the solvent can be introduced in a gaseous form into the reactor.

The molar ratio of ammonia to cyclohexanol and/or cyclohexanone is generally from 0.5/1 to 10/1, preferably from 1/1 to 5/1. When the amination reaction is preformed in the presence of molecular hydrogen, the molar ratio of hydrogen to cyclohexanol and/or cyclohexanone is generally from 0.01/1 to 10/1, preferably from 0.5/1 to 5/1. The reaction can be performed under reduced pressure, under atmospheric pressure or under superatmospheric pressure. When the reaction is performed under superatmospheric pressure, the reaction pressure is generally from 0.1 to 20 MPa, preferably from 1 to 10 MPa. The reaction temperature is generally from 50 to 300° C., preferably from 80 to 250° C. The reaction time depends on the desired level of the selectivity for and yield of cyclohexylamine as the end product and, hence, is not specifically limited. How-ever, the reaction time is generally from several seconds to several hours.

The amount of the amination catalyst depends on the type of the catalyst and the like, and is not specifically limited so long as a desired effect can be achieved by the use of the catalyst. However, the amount of the amination catalyst is generally from 0.0001/1 to 100/1, preferably from 0.001/1 to 50/1, in terms of the weight ratio of the catalyst to the starting material (cyclohexanol and/or cyclohexanone).

When the reaction is preformed in a gaseous phase, it is preferred to use an upflow reactor or a downflow reactor. In this case, the liquid hourly space velocity (LHSV) is preferably from 0.01 to 10 liters per hour per liter of the catalyst, more preferably from 0.05 to 5 liters per hour per liter of the catalyst.

The type of the by-product ($\alpha$) formed in the amination reaction in the step (1) varies depending on the type of the starting material, the type of the catalyst used and the like. In general, when cyclohexanol is used as the starting material in the step (1), the by-product ($\alpha$) comprises at least one. compound selected from the group consisting of cyclohexanone, N-(cyclohexylidene)-cyclohexylamine, dicyclohexylamine, cyclohexylaniline and aniline; when cyclohexanone is used as the starting material in the step (1), the by-product ($\alpha$) comprises at least one compound selected from the group consisting of cyclohexanol, N-(cyclohexylidene)-cyclohexylamine, dicyclohexylamine, cyclohexylaniline and aniline; and when a mixture of cyclohexanol and cyclohexanone is used as the starting material in the step (1), the by-product ($\alpha$) comprises at least one compound selected from the group consisting of cyclohexanol, cyclohexanone, N-(cyclohexylidene)-cyclohexylamine, dicyclohexylamine, cyclohexylaniline and aniline.

The cyclohexylamine produced can be recovered from the reaction mixture in the reactor as follows. The amination catalyst is separated from the reaction mixture. Then, to the resultant mixture is added cyclohexane, benzene or the like, followed by azeotropic distillation to recover the cyclohexylamine. If desired, the cyclohexylamine is further subjected to treatment for isolation, thereby obtaining a cyclohexylamine having a desired purity. Alternatively, the by-product ($\alpha$) is not separated from the reaction mixture, and a mixture of the cyclohexylamine produced and the by-product ($\alpha$) is subjected to a partial oxidation reaction in the step (2). In this case, the by-product ($\beta$) formed in the step (2) must be recycled to the step (1). The purity of the cyclohexylmine subjected to a partial oxidation in the step (2) is preferably 80% or more, more preferably 95% or more, most preferably 99% or more.

With respect to the step (2) of the method of the present invention, an explanation is made below. As a process for realizing the step (2) of subjecting the cyclohexylamine obtained in the step (1) to a partial oxidation reaction to obtain cyclohexanone oxime, there can be mentioned a process comprising reacting cyclohexylamine with an oxidizing agent in the presence of a catalyst. Examples of oxidizing agents used in the partial oxidation of cyclohexylamine include oxygens, such as molecular oxygen and ozone; inorganic hydroperoxides, such as hydrogen peroxide, peracetic acid and $K_2S_2O_8$; organic hydroperoxides, such as t-butylhydroperoxide, cumenehydroperoxide, ethylbenzenehydroperoxide and cyclohexylhydroperoxide; and oxygen acids, such as NaClO, NaBrO, PhIO and $NaIO_4$. Of these oxidizing agents, molecular oxygen and hydrogen peroxide are preferred, and molecular oxygen is more preferred. Molecular oxygen is generally used in the form of a mixture thereof with air or an inert gas, such as nitrogen or helium. The oxygen concentration in this mixture is preferably from 2 to 23%, more preferably from 3 to 11%. It is preferred that the oxygen concentration is controlled so as not to cause explosion in the reaction system.

As the catalyst used in the partial oxidation of cyclohexylamine, there can be used various metals, metal oxides, metal salts and organometal compounds. The type of the catalyst depends on the oxidizing agent used for the partial oxidation. The partial oxidation of cyclohexylamine can be performed by conventional processes. As examples of conventional processes for partial oxidation of cyclohexylamine using molecular oxygen as an oxidizing agent, there can be mentioned a process in which the partial oxidation of cyclohexylamine is performed in a liquid phase using, as a catalyst, a compound of at least one metal selected from the group consisting of metals belonging to Group 4 of the Periodic Table (i.e., Ti, Zr and Hf) (see Unexamined Japanese Patent Application Laid-Open Specification No. Hei 2-295956 (corresponding to EP 395046)); and a process in which the partial oxidation of cyclohexylamine is performed in a gaseous phase in the presence of a solid catalyst comprising $SiO_2$ gel, $\gamma$-$Al_2O_3$, and optionally $WO_3$ (see U.S. Pat. Nos. 4,337,358 and 4,504,681). As examples of conventional processes for partial oxidation of cyclohexylamine using hydrogen peroxide as an oxidizing agent, there can be mentioned a process using a catalyst comprising at least one metal selected from the group consisting of Mo, W and U (see U.S. Pat. No. 2,706,204); a process in which a titanium silicalite or a vanadium silicalite is used as a catalyst (see Tetrahedron (published by Elsevier Science Press, Netherlands), Vol. 51 (1995), No. 41, page 11305; and Catal. Lett. (published by Kluwer Publishers, Netherlands), Vol. 28 (1994), page 263. As examples of conventional processes for partial oxidation of cyclohexylamine using an organic hydroperoxide as an oxidizing agent, there can be mentioned a process using a catalyst comprising at least one metal selected from the group consisting of Ti, V, Cr, Se, Zr, Nb, Mo, Te, Ta, W, Re and U (see U.S. Pat. No. 3,960,954).

The partial oxidation reaction of cyclohexylamine can be performed in a gaseous or liquid phase using a fixed-bed or slurry-bed reactor. The reaction can be performed in a continuous or batchwise manner. When the reaction is performed in a liquid phase, a solvent can be used. With respect to the solvent, there is no particular limitation. Examples of solvents include those which are described in the above-mentioned patent documents, such as Unexamined Japanese Patent Application Laid-Open Specification No. Hei 2-295956 (corresponding to EP 395046) and U.S. Pat. No. 2,706,204. Specific examples of such solvents include $C_1$–$C_{10}$ alcohols (such as methanol and t-butanol), acetonitrile, benzene, toluene, dimethylformamide, dimethyl sulfoxide, triethylamine, dimethoxyethane, dioxane, diglyme and water. When the partial oxidation reaction is performed in the presence of a solvent, the amount of cyclohexylamine is generally from 1 to 30% by weight, preferably from 5 to 20% by weight, based on the total weight of cyclohexylamine and the solvent.

When the partial oxidation reaction is performed in a gaseous phase, the concentration of cyclohexylamine is preferably from 0.5 to 20% by volume, more preferably from 2 to 10% by volume, based on the total volume of the gases used. Cyclohexylamine alone may be introduced into the reactor. Alternatively, cyclohexylamine may be used in a diluted form. Specifically, cyclohexylamine may be used in the form of a mixture thereof with an inert gas (such as nitrogen or helium) which does not adversely affect the partial oxidation reaction. Further, the solvent can be introduced in a gaseous form into the reactor.

The reaction conditions can be appropriately determined, taking into consideration the type of the oxidizing agent used, the type of the catalyst used and the like. The reaction can be performed under reduced pressure, under atmospheric pressure or under superatmospheric pressure, and there is no particular limitation with respect to the total pressure of the reaction system. The reaction temperature is preferably from 20 to 300° C., more preferably from 80 to 250° C. When the reaction temperature is higher than 300° C., disadvantages are likely to occur wherein decomposition or overoxidation of the obtained cyclohexanone oxime is promoted. On the other hand, when the reaction temperature is lower than 20° C., disadvantages are likely to occur wherein the reaction rate is lowered. The reaction time depends on the desired level of the selectivity for and yield of cyclohexanone oxime as the end product and, hence, is not specifically limited. However, the reaction time is generally from several seconds to several hours.

The amount of the catalyst depends on the type of the catalyst and the like, and is not specifically limited so long as a desired effect can be achieved by the use of the catalyst. However, the amount of the catalyst is generally from 0.0001/1 to 100/1, preferably from 0.001/1 to 50/1, in terms of the weight ratio of the catalyst to cyclohexylamine.

When the reaction is preformed in a gaseous phase, it is preferred to use an upflow reactor or a downflow reactor. In this case, the liquid hourly space velocity (LHSV) is preferably from 0.01 to 10 liter per hour per liter of the catalyst, more preferably from 0.05 to 5 liter per hour per liter of the catalyst.

In general, the by-product ($\beta$) formed in the partial oxidation in the step (2) comprises at least one compound selected from the group consisting of cyclohexanone, nitrocyclohexane, N-(cyclohexylidene)-cyclohexylamine and dicyclohexylamine.

By the above-mentioned partial oxidation reaction of cyclohexylamine, cyclohexanone oxime is obtained in a reaction mixture in the reactor. The obtained cyclohexanone oxime can be recovered from the reaction mixture in the reactor as follows. The catalyst is separated from the reaction mixture. Then, from the resultant mixture is recovered the cyclohexanone oxime by a customary method, such as distillation or extraction. If desired, the cyclohexanone oxime is further subjected to treatment for isolation, thereby obtaining a cyclohexanone oxime having a desired purity. In this case, it is preferred that a purity of the obtained cyclohexanone oxime is 99% or more.

In the present invention, the above-mentioned by-product ($\alpha$) formed in the step (1) and/or by-product ($\beta$) formed in the step (2) are/is recycled to a reaction system of the amination reaction in the step (1) and then converted to cyclohexylamine. Thus, the by-product ($\alpha$) and/or by-product ($\beta$) can be considered to have the same value as that of the raw material subjected to an amination reaction or an intermediate product (i.e., cyclohexylamine) in the production of cyclohexanone oxime. By virtue of the recycling of such valuable by-product(s), the selectivity for cyclohexanone oxime as a desired product can be improved. In the present invention, the by-product (α) formed in the step (1) may be the same as the by-product (β) formed in the step (2). In this case, both or one of these by-products (α) and (β) may be recycled to a reaction system of the amination reaction in the step (1). For example, when each of the by-products (α) and (β) is dicyclohexylamine, both or one of the dicyclohexylamine as by-product (α) and the dicyclohexylamine as by-product (β) may be recycled to a reaction system of the amination reaction in the step (1).

In the reaction system of the amination reaction in the step (1), the conversion of the above-mentioned starting material and by-products to cyclohexylamine proceeds in such a manner as shown in the following reaction formulae (I) to (VIII), wherein formula (I) shows the amination of cyclohexanol, formula (II) shows the amination of cyclohexanone; formula (III) shows the amination of nitrocyclohexanone; formula (IV) shows the amination of dicyclohexylamine; formulae (V) and (VI) show the amination of N-(cyclohexylidene)-cyclohexylamine; formula (VII) shows the amination of cyclohexylaniline; and formula (VIII) shows the amination of aniline:

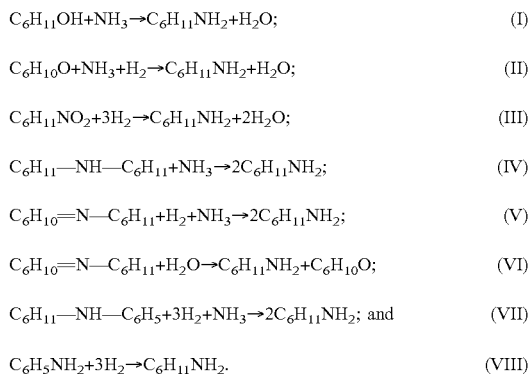

The separation of the by-product (α) produced in the amination reaction of the step (1) and/or by-product (β) produced in the partial oxidation reaction of the step (2) from the reaction mixture and the recycling thereof to the amination reaction system in the step (1) can be performed by conventional methods. For example, the separation and recycling of the above-mentioned by-product(s) can be performed as follows. Firstly, with respect to the method for separating and recycling the by-product (α), an explanation is made below. When the by-product (α) comprises two or more of the above-mentioned compounds, at least one of the compounds as the by-product (α) may be separated and recycled. However, it is especially preferred that all of the compounds as the by-product (α) are separated and recycled. Specific examples of methods for separating and recycling the by-product (α) include a method comprising subjecting a reaction mixture obtained by the amination reaction to distillation to thereby separate cyclohexylamine, removing from the resultant residue an undesirable component(s) (tar-like compound(s) having a high boiling point) which adversely affect(s) the amination reaction in the step (1) by a conventional method (e.g., distillation, extraction or the like), recycling resultant (containing the by-product (α)) to the reaction system of the amination reaction in the step (1); and a method comprising subjecting a reaction mixture obtained by amination reaction to distillation to thereby separate cyclohexylamine, separating from the resultant residue at least one compound as the by-product (α) by a conventional method (e.g., distillation, extraction or the like), and recycling the separated compound(s) to the reaction system of the amination reaction in the step (1). In the amination reaction in the step (1), water is by-produced as well as the by-product (α). The by-produced water may be recycled to the reaction system of the amination reaction in the step (1) with the by-product (α), or be separated from the by-product (α).

Next, an explanation is made below with respect to the method for separating and recycling the by-product (β). In general, the by-product (β) comprises two or more of the above-mentioned compounds. In such a case, at least one of the compounds as the by-product (β) may be separated and recycled. However, it is especially preferred that all of the compounds as the by-product (β) are separated and recycled. Specific examples of methods for separating and recycling the by-product (β) include a method comprising subjecting a reaction mixture obtained by a partial oxidation reaction of cyclohexylamine to distillation to thereby separate cyclohexanone oxime, removing from the resultant residue any undesirable component(s) (tar-like compound(s) having a high boiling point) which adversely affect(s) the amination reaction in the step (1) by a conventional method (e.g., distillation, extraction or the like), and recycling the resultant (containing the by-product (β)) to the reaction system of the amination reaction in the step (1); and a method comprising subjecting a reaction mixture obtained by a partial oxidation reaction of cyclohexylamine to distillation to thereby separate cyclohexanone oxime, separating from the resultant residue at least one compound as the by-product (β) by a conventional method (e.g., distillation, extraction or the like), and recycling the separated compound to the reaction system of the amination reaction in the step (1). In the partial oxidation reaction in the step (2), water is by-produced as well as the by-product (β). The by-produced water may be recycled to the reaction system of the amination reaction in the step (1) with the by-product (β), or be separated from the by-product (β).

When the reaction mixture obtained in the amination reaction of step (1) contains any of the starting material (i.e., cyclohexanol and/or cyclohexanone), ammonia and hydrogen if any which remain unreacted, it is preferred that the unreacted substance(s) is/are recycled to the reaction system of the amination reaction in the step (1). In such a case, the above-mentioned unreacted substance(s) may be recycled separately from or together with the by-product (α) and/or the by-product (β).

Further, when the reaction mixture obtained in the partial oxidation reaction of the step (2) contains cyclohexylamine and/or oxygen which remain(s) unreacted, it is preferred that the unreacted substance(s) is/are recycled to the reaction system of the partial oxidation reaction in the step (2).

The by-product (α) and by-product (β) can be recycled to the reaction system of the amination reaction in the step (1) individually or in combination.

With respect to the step (1) and step (2) of the present invention, there is a case where a by-product which can be recycled to the step (1) is not produced in either step (1) or step (2), i.e., only one of the by-product (α) and the by-product (β) is obtained. In such a case, the obtained recyclable by-product (the by-product (α) produced in the step (1) or the by-product (β) produced in the step (2)) needs to be recycled to the step (1).

In the present invention, cyclohexanol and/or cyclohexanone which are/is used as the starting material in the amination reaction in the step (1) can be produced by the conventional methods described above under "Prior art". However, it is recommended to use cyclohexanol produced by a method in which benzene is subjected to partial hydrogenation to obtain cyclohexene, and the obtained cyclohexene is subjected to hydration to obtain cyclohexanol, and/or cyclohexanone produced by subjecting the thus obtained cyclohexanol to dehydrogenation. The use of the thus obtained cyclohexanol and/or cyclohexanone in the production of cyclohexanone oxime is advantageous in that the total carbon yield in terms of the total yield with respect to useful compounds (including cyclohexane) obtained in the steps for producing cyclohexanone oxime as the end product from benzene as a starting material is advantageously high as compared to the case where cyclohexanol and/or cyclohexanone, which are/is produced by method(s) other than mentioned above, are/is used. Further, the use of the above-mentioned recommended cyclohexanol and/or cyclohexanone is also advantageous in that cyclohexanone oxime can be produced with less consumption of hydrogen, and that by-products which are difficult to separate are not formed.

Hereinbelow, an explanation is made with respect to the method for producing cyclohexene by partial hydrogenation of benzene and the method for producing cyclohexanol by hydration of cyclohexene. Further, the production of cyclohexanone by dehydrogenation of the obtained cyclohexanol can be performed by conventional dehydrogenation methods.

The partial hydrogenation of benzene can be performed by conventional processes. Examples of such conventional processes include a process using a catalyst composition comprising water, an alkali metal and at least one metal selected from the group consisting of metals belonging to Groups 8, 9 and 10 of the Periodic Table (see Examined Japanese Patent Application Publication No. Sho 56-22850 (corresponding to U.S. Pat. No. 3,376,720)); a process using a ruthenium as a catalyst and an alcohol or ester as an additive, wherein the ruthenium catalyst is supported on an oxide of nickel, cobalt, chromium, titanium or zirconium (see Examined Japanese Patent Application Publication No. Sho 52-3933); a process in which the partial hydrogenation of benzene is performed in the presence of ruthenium as a catalyst and a neutral or acidic solution containing a salt of at least one metal selected from the group consisting of manganese and metals belonging to Groups 1 and 2 of the Periodic Table (see Examined Japanese Patent Application Publication No. Sho 57-7607 (corresponding to U.S. Pat. No. 4,055,512)); a process in which the partial hydrogenation of benzene is performed in the presence of a catalyst, water and cobalt sulfate, wherein the catalyst comprises an oxide (such as silica or alumina) having carried thereon a substance comprised mainly of ruthenium (see Unexamined Japanese Patent Application Laid-Open Specification No. Sho 57-130926); a process in which the partial hydrogenation of benzene is performed in the presence of a catalyst, a metal sulfate and water, wherein the catalyst comprises barium sulfate having carried thereon ruthenium and at least one metal selected from the group consisting of iron, cobalt, silver and copper, and the metal contained in the metal sulfate is at least one metal selected from the group consisting of lithium, cobalt, iron and zinc (see Examined Japanese Patent Application Publication No. Hei 2-59811 (corresponding to U.S. Pat. No. 4,575,572 and EP 170915)); a process in which the partial hydrogenation of benzene is performed in the presence of a catalyst, water and at least one metal oxide, wherein the catalyst comprises barium sulfate having carried thereon ruthenium, and the metal oxide is selected from the group consisting of silicon dioxide, titanium dioxide and aluminum oxide (see Examined Japanese Patent Application Publication No. Hei 6-4545 (corresponding to U.S. Pat. No. 4,665,274 and EP 214530)); a process in which the partial hydrogenation of benzene is performed in the presence of a catalyst, water and at least one zinc compound, wherein the catalyst comprises metallic ruthenium crystals having an average crystallite size of 200 Å or less and/or an aggregate thereof (see Examined Japanese Patent Application Publication No. Hei 2-19098); a process in which the partial hydrogenation of benzene is performed in an acidic liquid phase in the presence of a hydrogenation catalyst, water, at least one water-soluble zinc compound, and hydrogen as a reducing agent (hydrogenating agent), wherein the catalyst comprises crystals (having an average crystallite size of 200 Å or less) and is obtained by subjecting a ruthenium compound containing a zinc compound to reduction treatment, wherein the amount of zinc in the catalyst is from 0.1 to 50% by weight, based on the weight of ruthenium in the catalyst, and wherein the catalyst is used in a non-supported form (see Examined Japanese Patent Application Publication No. Hei 2-16736); and a process in which the partial hydrogenation of benzene is performed in a neutral or acidic liquid phase in the presence of particles as a hydrogenation catalyst, water, a solid, basic zinc sulfate and at least one compound selected from the group consisting of a zirconium oxide and a hafnium oxide, wherein the particle catalyst is comprised mainly of metallic ruthenium having an average crystallite size of 200 Å or less (see Examined Japanese Patent Application Publication No. Hei 3-5371 (corresponding to U.S. Pat. No. 4,734,536 and EP 220525)).

As the catalyst for the partial hydrogenation of benzene, it is preferred to use a hydrogenation catalyst comprising at least one metal selected from the group consisting of metals belonging to Groups 8, 9 and 10 of the Periodic Table. Of the metals belonging to Groups 8, 9 and 10 of the Periodic Table, ruthenium is especially preferred. Examples of raw materials for hydrogenation catalysts include halides, nitrates, hydroxides, complexes and alkoxides. The hydrogenation catalyst may contain another metal as an auxiliary catalyst. As the auxiliary catalyst, effectively used are chromium, manganese, iron, cobalt, nickel, copper, zinc, silver, cadmium, gold and the like. Of these, zinc is especially preferred. When the catalyst contains an auxiliary catalyst as well as ruthenium, the atomic ratio of the metal used as an auxiliary catalyst to ruthenium is generally from 0.01 to 20, preferably from 0.1 to 10.

The hydrogenation catalyst may be used in such a form as supported on an oxide of a single metal (such as silica, alumina, zirconia or titania), a compound oxide of at least two of such metals, barium sulfate, calcium carbonate, diatomaceous earth, a zeolite or an activated carbon. Alternatively, the hydrogenation catalyst may be used in a non-supported form. From the viewpoint of improving the selectivity for cyclohexene, as the hydrogenation catalyst, it is preferred to use metallic ruthenium in a non-supported form.

The metallic ruthenium in a non-supported form is a reduction product obtained by reducing a ruthenium compound in a gaseous or liquid phase in the presence of an appropriate reducing agent, such as hydrogen, wherein the ruthenium is reduced to a metallic form thereof. The smaller the average crystallite size of the metallic ruthenium as a reduction product, the more advantageous to the production of cyclohexene. Specifically, from the viewpoint of improving the selectivity for cyclohexene, the average crystallite size of the metallic ruthenium is generally 200 Å or less, preferably 100 Å or less. The average crystallite size of the metallic ruthenium is calculated by the Scherrer formula using the breadth of diffraction peaks obtained by analyzing the metallic ruthenium by a general method, i.e., X-ray diffractometry. In the present invention, it is also preferred to use metallic ruthenium containing a zinc compound, which is prepared in substantially the same manner as explained above.

The amount of the hydrogenation catalyst depends on the type of the catalyst and the like; however, the amount of the catalyst is generally from 0.0001/1 to 100/1, preferably from 0.001/1 to 50/1, in terms of the weight ratio of the catalyst to benzene.

When metallic ruthenium in a non-supported form is used as the hydrogenation catalyst, the hydrogenation reaction can be performed in the presence of a zirconium oxide and/or a hafnium oxide, as well as the hydrogenation catalyst. The weight of the oxide(s) is from $1 \times 10^{-3}$ to 0.3 time that of water contained in the reaction system, preferably from $1 \times 10^{-2}$ to 0.1 time that of the water. The use of the oxide(s) is effective not only in that the selectivity for and yield of cyclohexene can be improved, but also in that adherence of the hydrogenation catalyst to the surface of the reactor, cohesion of the hydrogenation catalyst and the like can be suppressed.

In the partial hydrogenation of benzene, water is needed. It is preferred that water is used in an amount such that an organic phase comprised mainly of benzene and cyclohexene produced and an aqueous phase containing water are formed. Specifically, it is preferred that the amount of water is from 0.001 to 100% by weight, more advantageously from 0.5 to 20% by weight, based on the weight of benzene.

In the present invention, it is preferred that the partial hydrogenation of benzene is performed in the presence of a water-soluble metal compound as well as the hydrogenation catalyst and water. Examples of water-soluble metal compounds include acetic acid salts of metals, chlorides of metals, nitric acid salts of metals, sulfuric acid salts of metals and phosphoric acid salts of metals, wherein the metals are selected from metals belonging to Groups 1, 2 and 12 of the Periodic Table, chromium, manganese, iron, cobalt, nickel, copper and the like. Of these compounds, preferred are chlorides and sulfuric acid salts of metals belonging to Groups 1 and 2 of the Periodic Table and zinc, and more preferred are strong acid salts, such as zinc sulfate. Zinc sulfate can be used in the form of an aqueous solution thereof, wherein the concentration of zinc sulfate in the aqueous solution is from 0.01% by weight to the concentration of saturation. The concentration of zinc sulfate is preferably from 0.1 to 30% by weight.

Solid, basic sulfuric acid salts of the above-mentioned metals can be used in the partial hydrogenation of benzene. As such a solid, basic sulfuric acid salt, it is preferred to use a solid, basic zinc sulfate. The term "solid, basic zinc sulfate" means a compound represented by formulae, such as $ZnSO_4 \cdot mZnO \cdot nH_2O$ and $ZnSO_4 \cdot mZn(OH)_2$, wherein $0.5 \leq m \leq 4$ and $0 \leq n \leq 8$; and $Zn_{(l+1)}(OH)_2 \cdot lSO_4$, wherein $1 \leq l \leq 4$. Specific examples of such compounds include $ZnSO_4 \cdot 0.5ZnO$, $ZnSO_4 \cdot ZnO \cdot H_2O$ ($ZnSO_4 \cdot Zn(OH)_2$), $Zn_2(OH)_2SO_4$, $ZnSO_4 \cdot 3ZnO$, $ZnSO_4 \cdot 3ZnO \cdot 3H_2O$ ($ZnSO_4 \cdot 3Zn(OH)_2$), $ZnSO_4 \cdot 3ZnO \cdot 6H_2O$, $ZnSO_4 \cdot 3ZnO \cdot 7H_2O$, $ZnSO_4 \cdot 3ZnO \cdot 8H_2O$ and $ZnSO_4 \cdot 4ZnO \cdot 4H_2O$ ($ZnSO_4 \cdot 4Zn(OH)_2$). Further examples of solid, basic zinc sulfates are enumerated, for example, in "Mukikagaku Zensho (Encyclopedia of Inorganic Chemistry)", VIII-1, page 500, published by Maruzen Co., Ltd., Japan.

The above-mentioned types of solid, basic zinc sulfate have conventionally been known and can be produced by various processes. As a well-known conventional process for producing a solid, basic zinc sulfate, there can be mentioned a process comprising reacting zinc sulfate as a mother liquor with an alkali, optionally followed by heating. Alternatively, a solid, basic zinc sulfate can be produced by a process comprising adding zinc hydroxide to aqueous sulfuric acid or aqueous zinc sulfate, followed by heating. In each of these processes, the solid, basic zinc sulfate is obtained in the form of a mixture comprising various types of solid, basic zinc sulfate. Basic sulfuric acid salts of metals belonging to Groups 1, 2 and 12 of the Periodic Table, chromium, manganese, iron, cobalt, nickel, copper and the like can also be produced in substantially the same manner as explained above.

The solubility of the solid, basic zinc sulfate in water is small and, hence, even a very small amount of solid, basic zinc sulfate can be present in a solid form in a reaction system for partial hydrogenation of benzene. In the partial hydrogenation of benzene in the present invention, the amount of solid, basic zinc sulfate is generally from $1 \times 10^{-5}$ to 1, preferably from $1 \times 10^{-4}$ to 0.5, in terms of the weight ratio of zinc contained in the solid, basic zinc sulfate to the hydrogenation catalyst.

It is preferred that the reaction system for the partial hydrogenation of benzene contains an aqueous zinc sulfate and/or solid, basic zinc sulfate. The pH value of the reaction system depends on the amount of the above-mentioned zinc compound and the like; however, the reaction system is preferably neutral, or slightly weakly basic or acidic, more preferably neutral or acidic. Specifically, the pH value of the reaction system is preferably from 1 to 7, more preferably from 4 to less than 7.

The partial hydrogenation reaction of benzene is generally performed in a liquid phase using a slurry-bed reactor, in a continuous or batchwise manner. The reaction can also be performed using a fixed-bed reactor. The reaction conditions are appropriately determined, taking into consideration the type and amount of the catalyst used, the type and amount of the additive used, and the like. The pressure of hydrogen is generally from 0.1 to 20 MPa, preferably from 1 to 10 MPa. The reaction temperature is generally from room temperature to 250° C., preferably from 100 to 200° C. The reaction time depends on the desired level of the selectivity for and yield of cyclohexene and, hence, is not specifically limited. However, the reaction time is generally from several seconds to several hours.

Accordingly, in the present invention, it is especially preferred that the partial hydrogenation of benzene is performed in a neutral or acidic liquid phase in the presence of (a) a hydrogenation catalyst which comprises metallic ruthenium having an average crystallite size of 200 Å or less and optionally a zinc compound, (b) water, and (c) at least one compound selected from the group consisting of a zirconium oxide, a hafnium oxide, a water-soluble zinc compound and solid, basic zinc sulfate, wherein the hydrogenation catalyst is used in a non-supported form.

The partial hydrogenation reaction of benzene is generally performed in a four-phase system comprising an aqueous phase containing water, a solid phase containing the hydrogenation catalyst present in the aqueous phase, an oil phase comprising the raw materials and the products, and a gaseous phase containing molecular hydrogen, wherein the partial hydrogenation reaction advances in a slurry of these four phases. The resultant reaction liquid is phase-separated into an aqueous phase containing the hydrogenation catalyst and an oil phase containing the cyclohexene produced, the benzene remaining, unreacted, and the like. The oil phase is separated from the aqueous phase, and provided to a separation step. The aqueous phase containing the hydrogenation catalyst can be recycled as a catalyst slurry to the reactor. In the partial hydrogenation reaction of benzene, generally, cyclohexane is produced as a by-product as well as cyclohexene as the end product. In this case, the oil phase contains cyclohexene, cyclohexane and benzene. Since the boiling points of these compounds are very close to each other, separation of these compounds is conducted by extractive distillation or azeotropic distillation. If desired, the separated cyclohexene can be further subjected to treatment for isolation, thereby obtaining a cyclohexene having a desired purity. In such a case, it is preferred that the obtained cyclohexene has a purity of 99% or more. In general, it is preferred that the unreacted benzene which is separated from cyclohexene and cyclohexane is recycled to the reactor.

Next, an explanation is made below with respect to the process for producing cyclohexanol by hydration of cyclohexene. The hydration of cyclohexene can be performed by conventional processes. Examples of conventional processes for hydrating cyclohexene include a process in which the hydration of cyclohexene is performed using a mineral acid, especially sulfuric acid (see Examined Japanese Patent Application Publication No. Sho 48-447); a process using an aromatic sulfonic acid (see Examined Japanese Patent Application Publication No. Sho 43-8104 and Examined Japanese Patent Application Publication No. Sho 43-16123 (corresponding to DE 1230793)); a process using a heteropoly acid, such as phosphotungstic acid or phosphomolybdic acid (see Unexamined Japanese Patent Application Laid-Open Specification No. Sho 53-9746); a process using an ion exchange resin (see Examined Japanese Patent Application Publication Nos. Sho 38-15619 and Sho 44-26656); a process usually employed for hydration of olefins, in which a mordenite, a clinoptilolite or a zeolite having a faujasite structure, which is dealkalized, is used (see Examined Japanese Patent Application Publication No. Sho 47-45323); and a process using ZSM-5, which is a crystalline aluminosilicate (see Unexamined Japanese Patent Application Laid-Open Specification No. Sho 58-194828).

Examples of catalysts for hydrating cyclohexene include the acid catalysts used in the above-mentioned conventional processes. As the hydration catalyst, a zeolite is preferred. With respect to the type of the zeolite, there is no particular limitation so long as the zeolite can be used as a catalyst. Examples of zeolites as a hydration catalyst include an aluminosilicate, a metallosilicate, a silicalite, an aluminophosphate and a metallophosphate, each of which may have various structures. Further examples of zeolites include modified zeolites obtained by subjecting the above-mentioned zeolites to acid treatment, heat treatment or dealumination treatment. The zeolite used as the hydration catalyst in the present invention is generally a proton exchanged zeolite (H form zeolite). A part of the zeolite may be replaced by at least one cation species selected from the group consisting of alkali metals (such as Na, K and Li), alkaline earth metals (such as Mg, Ca and Sr) and rare earth metals (such as La and Ce).

It is especially preferred that the zeolite is selected from the group consisting of zeolites of ZSM-5 family, which are crystalline aluminosilicates (hereinafter, this zeolite is frequently referred to simply as "ZSM-5"). Zeolites of ZSM-5 family were developed by Mobil Oil, U.S.A. (see U.S. Pat. No. 3,702,886). An ZSM-5 is unique in the following points. In the ZSM-5, the $SiO_2/Al_2O_3$ molar ratio is 20 or more. Further, three-dimensional pores having an inlet of a ten-membered oxygen ring are present in the crystalline structure of the ZSM-5. In the present invention, with respect to the cation contained in the ZSM-5 (which is a crystalline aluminosilicate), it is preferred that the cation is selected from the group consisting of a proton, cations of alkaline earth metals (such as Mg, Ca and Sr) and cations of rare earth metals (such as La and Ce). Of these cations, a proton is most preferred.

The hydration reaction can be performed in a reaction system containing only cyclohexene and water. The hydration reaction can also be performed in a reaction system containing an organic solvent as well as cyclohexene and water. Examples of organic solvents include halogenated hydrocarbons, alcohols, ethers, sulfur compounds and ketones. Examples of halogenated hydrocarbons include methylene chloride, chloroform, tetrachloromethane, trichloroethane and tetrachloroethane; bromides, iodides and fluorides corresponding to the hydrocarbon chlorides mentioned above. Examples of alcohols include $C_1$–$C_{10}$ alcohols, such as methanol, ethanol, isopropanol, n-propanol, isobutanol and n-butanol. Examples of ethers include those which have one or a plurality of ether linkages, such as dioxane, tetrahydrofuran, diethyl ether, diisopropyl ether, diamyl ether, ethylene glycol, and diethylene glycol dimethyl ether. Examples of sulfur compounds include sulfones, such as dipropyl sulfone and sulfolane; and sulfoxides, such as dimethyl sulfoxide. Examples of ketones include acetone and methyl ethyl ketone. These organic solvents can be used individually or in combination.

In the hydration reaction of cyclohexene, the amount of water is preferably from 1 to 100, in terms of the molar ratio of water to cyclohexene. The amount of the hydration catalyst is preferably from 0.01 to 100, in terms of the weight ratio of the catalyst to cyclohexene. When an organic solvent is used, the amount of the organic solvent is preferably from 0.01 to 100, in terms of the volume ratio of the solvent to cyclohexene.

In the hydration reaction, the reaction temperature is generally from 50 to 300° C., preferably from 100 to 200° C. The reaction can be performed under reduced pressure, under atmospheric pressure or under superatmospheric pressure; however, it is preferred that the reaction is performed under superatmospheric pressure. The reaction time depends on the desired level of the selectivity for and yield of cyclohexanol as the desired intermediate and, hence, is not specifically limited. However, the reaction time is generally from several seconds to several hours.

With respect to the manner of the hydration reaction, there is no particular limitation; the reaction can be performed in either of continuous and batchwise manners. The hydration reaction is generally performed as follows. Cyclohexene is added to a catalyst slurry comprising a hydration catalyst and water to effect hydration of cyclohexene in a suspension state to obtain a reaction mixture comprising an aqueous phase comprised of the catalyst slurry and an oil phase comprised of cyclohexanol produced and the cyclohexene remaining unreacted. The oil phase is phase-separated from the aqueous phase, and provided to a separation step. The aqueous phase containing the hydration catalyst can be recycled as the catalyst slurry to the reactor. In the hydration reaction, a small amount of methylcyclopentene is generally formed as a by-product as well as cyclohexanol as the desired intermediate. The oil phase, which contains the cyclohexanol, the methylcyclopentene and the cyclohexene, is separated into a high boiling point component containing cyclohexanol and a low boiling point component containing cyclohexene by a customary method, such as distillation. If desired, the separated cyclohexanol can be further subjected to treatment for isolation, thereby obtaining a cyclohexanol having a desired purity. In such a case, it is preferred that the obtained cyclohexanol has a purity of 99% or more. In general, it is preferred that the unreacted cyclohexene which is separated from cyclohexanol is subjected to treatment for isolation so as to obtain cyclohexene having a desired purity, followed by recycling thereof to the reactor.

As explained above, by the method of the present invention, cyclohexanone oxime can be produced with high selectivity, using a simple apparatus, by a simple operation. Further, the method of the present invention is free from problems accompanying the prior art, such as generation of a by-product which is difficult to separate and which adversely affects the quality of ϵ-caprolactam produced from cyclohexanone oxime, and/or generation of a by-product (e.g., ammonium sulfate) which is of little commercial value. As explained above, the conventional method for producing cyclohexanone oxime by reacting cyclohexanone (obtained from benzene through cyclohexane) with a hydroxylamine salt has the following problems. The selectivity for cyclohexanone oxime is as low as 73 to 83%. Also, as by-products, carboxylic acids, alcohols, aldehydes, ketones, ethers, esters, hydrocarbons and the like are generated. These by-products cannot be converted into useful compounds even if recycled, so that the by-products are generally separated from the cyclohexanone oxime as the end product and discarded. Furthermore, by products (such as cyclohexyl butyl ether, n-pentylcyclohexane, cyclohexyl acetate and hexahydrobenzaldehyde) which are difficult to separate from the end product (i.e., cyclohexanone oxime) are inevitably generated. It is known that these undesired by-products still remain in a subsequent rearrangement step for producing ϵ-caprolactam from cyclohexanone oxime, leading to a lowering of the quality of ϵ-caprolactam. On the other hand, in the method of the present invention, such undesired by-products are not generated. Further, most of the by-products generated by the method of the present invention are recyclable, and with respect to the other by-products, which are not recyclable, most of them are useful compounds, such as cyclohexane, so that generation of wastes can be suppressed to an extremely low level. Such an effect of the method of the present invention is especially remarkable when cyclohexanone oxime is produced by a method comprising producing cyclohexene from benzene as a raw material and subjecting the obtained cyclohexene to hydration to produce cyclohexanol, subsequently producing cyclohexanone oxime from the produced cyclohexanol by performing the above-mentioned steps (1) and (2) of the method of the present invention. In this case, cyclohexanone oxime is produced by a method comprising the following steps (i) to (iv), wherein the by-products generated in the step (iii) and/or step (iv) are/is recycled to the step (iii):

(i) subjecting benzene to partial hydrogenation to produce cyclohexene, (ii) hydrating the produced cyclohexene to produce cyclohexanol, (iii) subjecting to amination the cyclohexanol produced in the step (ii), thereby obtaining cyclohexylamine, and (iv) subjecting the obtained cyclohexylamine to partial oxidation to obtain cyclohexanone oxime.

The raw materials, catalysts and reaction conditions employed in the steps (i) to (iv) are as described above.

With respect to the effects of the method of the present invention, a detailed explanation is made below. In the method of the present invention, when benzene is used as a raw material, cyclohexanone oxime can be produced with very high selectivity. Further, the following excellent effects are achieved.

The conventional method for producing cyclohexanone oxime by reacting cyclohexanone (obtained from benzene through cyclohexane) with a hydroxylamine salt is disadvantageous not only in that undesired by-products mentioned above are generated, but also in that about 20 to 30% by weight of the products are by-products which must be discarded as wastes. On the other hand, in the method of the present invention, when benzene is used as a raw material, not only can the generation of undesired by-products mentioned above be prevented, but also most of the by-products are recyclable. Further, about 95% by weight or more of the products generated in the method of the present invention are useful compounds, such as cyclohexanone oxime as the end product, and cyclohexane which is a useful by-product. Furthermore, in the method of the present invention, the amount of hydrogen consumed is very small as compared to the amount of hydrogen consumed in the above-mentioned conventional method. Therefore, the method of the present invention, in which benzene is used as a raw material, is very commercially advantageous.

BEST MODE FOR CARRYING OUT THE INVENTION

Hereinbelow, the present invention will be described in more detail with reference to the following Example and Comparative Example, which should not be construed as limiting the scope of the present invention.

EXAMPLE 1

1) Step of Subjecting Benzene to Partial Hydrogenation to Produce Cyclohexene 5.0 g of ruthenium chloride ($RuCl_3.3H_2O$) and 13.0 g of zinc chloride were dissolved in 500 ml of water, followed by stirring. To the resultant mixture was added 70 ml of a 30% by weight aqueous NaOH solution, followed by washing with a 1 N aqueous NaOH solution, thereby obtaining a black precipitate. The obtained black precipitate was dispersed in 500 ml of a 5% by weight aqueous NaOH solution. The resultant dispersion was charged into an autoclave having an inner volume of 1,000 ml, which was provided with a stirrer. Hydrogen gas was introduced into the autoclave so that the total pressure in the autoclave became 5 MPa. Then, a reduction reaction was effected at 150° C. for 12 hours in the autoclave, followed by washing and drying, thereby obtaining 2.3 g of a hydrogenation catalyst (a ruthenium catalyst). The amount of zinc in the hydrogenation catalyst was 7.4% by weight, based on the weight of ruthenium in the hydrogenation catalyst. The hydrogenation catalyst had an average crystallite size of 55 Å.

0.5 g of the above-obtained ruthenium catalyst, 2.5 g of $ZrO_2$ powder (average particle diameter: 0.35 μm), basic zinc sulfate ($ZnSO_4.3Zn(OH)_2$) containing 30 mg of zinc, and 280 ml of a 4% by weight aqueous $ZnSO_4$ solution were charged into an autoclave having an inner volume of 1,000 ml, which was made of titanium. The autoclave was purged with hydrogen gas while stirring, and the temperature in the autoclave was elevated to 150° C. 140 ml of benzene was introduced under superatmospheric pressure into the autoclave, and a partial hydrogenation reaction of benzene was effected under a total pressure of 5 MPa in the autoclave while vigorously stirring. 30 Minutes after the start of the reaction, the resultant reaction mixture was withdrawn from the autoclave, and the oil phase of the reaction mixture was analyzed by gas chromatography (GC). The results of the analysis of the oil phase of the reaction mixture by GC showed that the conversion of benzene was 42.3%, and the selectivity for cyclohexene was 86.5%. Further, it was found that, as a by-product, only cyclohexane was generated (selectivity: 13.4%).

The conditions for GC were as follows.

Apparatus: Gas chromatograph Model GC-14A, manufactured and sold by Shimadzu Corporation, Japan (this apparatus was provided with a flame ionization detector (FID))

Column: Capillary column ULBON HR-20M, manufactured and sold by Shinwa Chemical Industries, Ltd., Japan (inner diameter: 0.25 mm, length: 25 m)

Carrier gas: helium

Flow rate of an eluent: 20 ml/min

Temperature programming: the analysis was conducted at a constant temperature of 50° C.

The reaction mixture was subjected to an extraction distillation with N,N-dimethylacetamide as a solvent by means of a distillation apparatus, thereby obtaining a cyclohexene product having a purity of 99.5% or more.

2) Step of Hydrating Cyclohexene to Obtain Cyclohexanol 180 g of a 10% by weight aqueous solution of tetrapropylammonium hydroxide was added to 150 g of an aqueous silicate solution ($SiO_2$ concentration of the solution: 29.9% by weight). To the resultant mixture were added 4 g of aluminum nitrate ($Al(NO_3)_3 \cdot 9H_2O$) and 40 g of water, followed by stirring for 10 minutes. To the resultant mixture was dropwise added concentrated nitric acid while vigorously stirring to adjust the pH of the mixture to 10 to 10.5, thereby obtaining a uniform gel. The obtained gel was charged into an autoclave having an inner volume of 1,000 ml, which was provided with a stirrer, followed by stirring at 180° C. for 24 hours. The resultant was washed with a sufficient amount of an ion exchanged water, followed by drying at 120° C. for 10 hours, thereby obtaining a product. The obtained product was analyzed by X-ray diffractometry, and identified as ZSM-5. The product was also examined by X-ray fluorescence analysis, and it was found that, in the product, the silica/alumina molar ratio was 60.

The product (i.e., ZSM-5) was calcined at 600° C. for 24 hours under air circulation. The resultant was subjected to an ion exchange using an aqueous solution of ammonium chloride, followed by calcination in air at 500° C. for 4 hours, thereby obtaining a catalyst. 280 g of water, 30 g of the cyclohexene obtained in the above-mentioned step 1), and 20 g of the above-obtained catalyst were charged into an autoclave having an inner volume of 1,000 ml, which was provided with a stirrer, to effect a reaction at 100° C. for 1 hour while stirring. The resultant reaction mixture was analyzed by GC. The analysis of the reaction mixture by GC showed that the conversion of cyclohexene was 12.4%, and the selectivity for cyclohexanol was 99.6%.

The conditions for GC were as follows.

Apparatus: Gas chromatograph Model GC-14A, manufactured and sold by Shimadzu Corporation, Japan (this apparatus was provided with a flame ionization detector (FID))

Column: Capillary column ULBON HR-20M, manufactured and sold by Shinwa Chemical Industries, Ltd., Japan (inner diameter: 0.25 mm, length: 25 m)

Carrier gas: helium

Flow rate of an eluent: 20 ml/min

Temperature programming: initially, the temperature was maintained at 50° C. for 5 minutes, then the temperature was elevated at a rate of 10° C./min to 230° C., and then the temperature was maintained at 230° C. for 5 minutes.

The reaction mixture was subjected to distillation to obtain a cyclohexanol product having a purity of 99.5% or more.

3-1) Step of Subjecting Cyclohexanol to Amination to Obtain Cyclohexylamine 47 g of copper nitrate trihydrate and 16 g of nickel nitrate hexahydrate were dissolved in 250 ml of water to obtain an aqueous solution. To the obtained aqueous solution was added 10 g of γ-alumina, followed by stirring. The resultant solution was heated in a water bath so that the temperature of the solution became 80° C. Then, 250 ml of an aqueous solution having dissolved therein 42 g of sodium carbonate was stepwise added to the above-obtained solution heated in the water bath over 2 hours while stirring. The resultant solution was aged for 5 hours, followed by filtration to thereby obtain a precipitate. The obtained precipitate was repeatedly washed with water, followed by drying thereof at about 100° C. for one day, thereby obtaining a dried precipitate. The obtained dried precipitate was placed in a mortar and pulverized using a pestle. The pulverized, dried precipitate was packed in a quartz tube, followed by calcination in an electric tubular furnace at 350° C. for 3 hours, thereby obtaining a copper-nickel/γ-alumina catalyst.

The above-obtained copper-nickel/γ-alumina catalyst was shaped to obtain a particulate copper-nickel/γ-alumina catalyst. The obtained particulate copper-nickel/γ-alumina catalyst was charged into a tubular reactor which was made of stainless steel. A hydrogen gas was introduced into the tubular reactor at a rate of 150 ml/min to effect an activation treatment of the catalyst for 3 hours while maintaining the catalyst phase at 350° C. After completion of the activation treatment, the temperature of the reactor was lowered to 180° C. and a gaseous mixture having a composition of cyclohexanol:ammonia:hydrogen=1:5:3 was introduced into the reactor under atmospheric pressure at an LHSV of 0.1 liter per hour per liter of the catalyst to effect a reaction for 5 hours, thereby obtaining a reaction mixture. The obtained reaction mixture was analyzed by GC. The results of the analysis of the re-action mixture by GC showed that the conversion of cyclohexanol was 96.3%, and the selectivity for cyclohexylamine was 98.7%. The by-products were dicyclohexylamine (selectivity: 0.8%) and cyclohexylaniline (selectivity: 0.4%).

The conditions for GC were as follows.

Apparatus: Gas chromatograph Model GC-14A, manufactured and sold by Shimadzu Corporation, Japan (this apparatus was provided with a flame ionization detector (FID))

Column: Capillary column DB-1701, manufactured and sold by J&W Scientific, Germany (inner diameter: 0.25 mm, length: 30 m)

Carrier gas: helium

Flow rate of an eluent: 20 ml/min

Temperature programming: initially, the temperature was maintained at 50° C. for 10 minutes, then the temperature was elevated at a rate of 10° C./min to 300° C., and then the temperature was maintained at 300° C. for 5 minutes.

The reaction mixture was subjected to distillation to obtain a cyclohexylamine product having a purity of 99.5% or more.

4) Step of Subjecting Cyclohexylamine to Partial Oxidation to Obtain Cyclohexanone Oxime 100 g of aluminum sec-butoxide was placed in a beaker. Then, into the beaker was stepwise charged an aqueous solution of ammonium metatungstate while vigorously stirring by means of a glass rod, wherein the aqueous solution of ammonium metatungstate was obtained by dissolving 7.0 g of commercially available ammonium metatungstate in 100 g of water. The resultant gel-like product was dried at room temperature for 1 hour, followed by vacuum drying at 120° C. overnight. The resultant, dried product was calcined at 400° C. for 4 hours under atmospheric pressure, thereby obtaining an alumina catalyst containing tungsten oxide. The obtained alumina catalyst was examined by X-ray fluorescence analysis. The results of the analysis of the alumina catalyst showed that the catalyst had a tungsten content of 21.8% by weight. The catalyst was subjected to compression molding, followed by pulverization, thereby obtaining a particulate catalyst. The particles of the catalyst were sieved to obtain catalyst particles having diameters in the range of from 1.0 to 1.4 mm. The obtained solid catalyst was used in the below-mentioned reaction.

The solid catalyst was charged into a tubular reactor having an inner diameter of 30 mm, which was made of stainless steel. The tubular reactor containing the solid catalyst was placed in a furnace. The reactor was purged with nitrogen gas, and then heated to 160° C. Then, a reaction gas containing 6.0% by volume of cyclohexylamine and 7.0% by volume of oxygen was introduced into the reactor at an LHSV of 0.1 liter per hour per liter of the catalyst, thereby effecting a reaction. Samples of the resultant gaseous reaction mixture were automatically withdrawn from the reactor, and analyzed by GC. The results of the analysis of the samples by GC showed that, when the reaction became steady, the conversion of cyclohexylamine was 29.2%, and the selectivity for cyclohexanone oxime was 87.5%. Further, it was found that, as by-products, cyclohexanone (selectivity: 2.1%), nitrocyclohexane (selectivity: 1.8%), N-cyclohexylidenecyclohexylamine (selectivity: 6.6%), dicyclohexylamine (selectivity: 0.9%) and the like were generated.

The analysis by GC was conducted in substantially the same manner as in the case of the amination of cyclohexanol in the above-mentioned step 3-1).

The reaction mixture was subjected to distillation to obtain a cyclohexanone oxime product having a purity of 99.5% or more.

3-2) Step of Subjecting a By-product/Cyclohexanol Mixture to Amination to Obtain Cyclohexylamine The reaction mixtures obtained in the above-mentioned steps 3-1) and 4) were subjected to distillation to separate the desired products and unreacted starting materials, thereby obtaining a distillate containing the following by-products: cyclohexanone (14.8% by weight), nitrocyclohexane (11.2% by weight), N-cyclohexylidenecyclohexylamine (47.2% by weight), dicyclohexylamine (21.1% by weight) and cyclohexylaniline (5.1% by weight). 12.1 g of the obtained distillate was mixed with 50 g of cyclohexanol. The resultant mixture (i.e., by-products/cyclohexanol mixture) was subjected to an amination reaction under substantially the same conditions as in the above-mentioned step 3-1). As a result, it was found that the conversion of the by-products/cyclohexanol mixture was 98.5% and the selectivity for cyclohexylamine was 97.4%. Dicyclohexylamine and cyclohexylaniline were formed as by-products and the selectivity for the by-products was not more than 2%.

In Example 1, cyclohexanone oxime was produced from benzene as a starting material. The method employed in Example 1 for producing cyclohexanone oxime included four steps in total (i.e., the step of partial hydrogenation of benzene, the step of hydrating cyclohexene, the step of amination of cyclohexanol, and the step of partial oxidation of cyclohexylamine). The by-products formed in the step of amination of cyclohexanol and in the step of partial oxidation of cyclohexylamine were recycled to the step of amination.

From the selectivities for various compounds produced in the steps of the method, the benzene-based selectivity for cyclohexanone oxime, and the total carbon yield in terms of the total yield with respect to useful compounds (i.e., cyclohexanone oxime and cyclohexane) were calculated by the following formulae:

Selectivity for cyclohexanone oxime (%)=(molar amount of cyclohexene produced/molar amount of benzene converted)×(molar amount of cyclohexanol produced/molar amount of cyclohexene converted)×(molar amount of cyclohexylamine produced/molar amount of cyclohexanol converted)×(molar amount of cyclohexanone oxime produced/molar amount of cyclohexylamine converted)×100

Total carbon yield (%)=(molar amount of cyclohexene produced/molar amount of benzene converted)×(molar amount of cyclohexanol produced/molar amount of cyclohexene converted)×(molar amount of cyclohexylamine produced/molar amount of cyclohexanol converted)×(molar amount of cyclohexanone oxime produced/molar amount of cyclohexylamine converted)×100+(molar amount of cyclohexane produced/molar amount of benzene converted)×100

When cyclohexanone oxime was produced without recycling the by-products to the step of amination reaction, the selectivity for cyclohexanone oxime was 74.4%, and the total carbon yield in terms of the total yield with respect to the useful compounds was 87.8% (74.4% (cyclohexanone oxime)+13.4% (cyclohexane)).

On the other hand, when cyclohexanone oxime was produced while recycling the by-products to the step of amination reaction, the selectivity for cyclohexanone oxime was 84.8%, and the total carbon yield in terms of the total yield with respect to the useful compounds was 98.2% (84.8% (cyclohexanone oxime)+13.4% (cyclohexane)).

Further, the cyclohexanone oxime produced through the above-mentioned steps contained no undesired impurity (such as butyl cyclohexyl ether, n-pentyl-cyclohexane, cyclohexyl acetate or hexahydrobenzaldehyde) which adversely affects the quality of ε-caprolactam produced from cyclohexanone oxime (ε-caprolactam is used as a raw material for producing nylon 6 or the like).

COMPARATIVE EXAMPLE 1

Cyclohexanone oxime was produced by a method in which cyclohexane obtained by complete hydrogenation of benzene is subjected to oxidation with air and then to dehydrogenation to obtain cyclohexanone, and the obtained cyclohexanone is subjected to oximation using hydroxylamine sulfate obtained by a method described in Unexamined Japanese Patent Application Laid-Open Specification No. Sho 58-50925 to thereby obtain cyclohexanone oxime. In this method, the production of cyclohexanone and the oximation of the produced cyclohexanone were performed as follows.

1) Step of Subjecting Cyclohexane to Oxidation with Air to Obtain a Mixture of Cyclohexanone and Cyclohexanol 600 g of cyclohexane and cobalt naphthenate as a catalyst (amount of the catalyst in terms of cobalt atom: 1 ppm by weight, based on the weight of cyclohexane) was charged into an autoclave having an inner volume of 1,000 ml, which was made of glass and had an inlet for gas. A gaseous mixture of oxygen and nitrogen ($O_2/N_2$ volume ratio: 1/9) was flowed to the autoclave at a rate of 1,000 ml/min (N.T.P., that is, under normal temperature and pressure conditions) to effect a reaction at 150° C. under 1 MPa for 40 minutes while stirring. Then, the resultant reaction mixture was allowed to stand still for 30 minutes while flowing nitrogen gas to the autoclave. Gas withdrawn from the autoclave, which entrained the reaction mixture, was cooled to separate the reaction mixture as a condensate from the gas. The condensate reaction mixture was returned to the autoclave. The gas having the reaction mixture removed therefrom was discarded as a waste. The reaction mixture was analyzed by GC. The results of the analysis of the reaction mixture by GC showed that the conversion of cyclohexane was 4.0%, and the total selectivity for cyclohexanol and cyclohexanone was 75.8% (the weight ratio of the produced cyclohexanol to the produced cyclohexanone was 6/4). The analysis by GC was conducted in substantially the same manner as in the case of the hydration of cyclohexene in the above-mentioned step 2) in Example 1.

Further, the reaction mixture was analyzed by GC under the below-mentioned conditions, and it was found that the reaction mixture contained, as by-products, a carboxylic acid, an aldehyde, a ketone other than cyclohexanone, an ester, an ether, an alcohol other than cyclohexanol, a hydrocarbon other than cyclohexane, and the like.

Apparatus: Gas chromatograph Model GC-14A, manufactured and sold by Shimadzu Corporation, Japan (this apparatus was provided with a flame ionization detector (FID))

Column: Capillary column DB-1701, manufactured and sold by J&W Scientific, Germany (inner diameter: 0.25 mm, length: 30 m)

Carrier gas: helium

Flow rate of an eluent: 20 ml/min

Temperature programming: initially, the temperature was maintained at 50° C. for 10 minutes, then the temperature was elevated at a rate of 10° C./min to 350° C., and then the temperature was maintained at 350° C. for 5 minutes.

The reaction mixture was washed with an alkali solution by a conventional method, followed by distillation by a conventional method to thereby remove the cyclohexane remaining unreacted and by-products, thereby obtaining a mixture containing cyclohexanol and cyclohexanone. From the mixture was removed cyclohexanone by distillation to obtain a distillation residue containing cyclohexanol. The distillation residue containing cyclohexanol was further subjected to dehydrogenation to obtain cyclohexanone. The obtained cyclohexanone was purified by distillation to obtain a purified cyclohexanone product having a purity of 99.5%. However, the purified cyclohexanone product contained, as impurities, 2,500 ppm by weight of butyl cyclohexyl ether, 500 ppm by weight of n-pentylcyclohexane, 450 ppm by weight of cyclohexyl acetate and 200 ppm by weight of hexahydrobenzaldehyde, wherein each of these impurities has a boiling point which is very close to that of cyclohexanone. It is well-known that these impurities remain not only in a subsequent step of oximation of the cyclohexanone for obtaining cyclohexanone oxime, but also in a rearrangement step for producing ε-caprolactam from the obtained cyclohexanone oxime, leading to a lowering of the quality of the produced ε-caprolactam.

2) Step of Subjecting Cyclohexanol to Dehydrogenation to Obtain Cyclohexanone

An oxide catalyst containing Cu and Cr in the form of particles was charged into a tubular reactor having an inner diameter of 30 mm, which was made of stainless steel. A gaseous mixture of hydrogen and nitrogen was introduced into the reactor to effect reduction treatment of the catalyst. The cyclohexanol obtained in the above-mentioned step 1) was vaporized with heat, and introduced into the reactor at an LHSV (liquid hourly space velocity) of 0.1 liter per hour per liter of the catalyst to effect a reaction under 0.12 MPa for 10 hours while maintaining each of the temperatures of an inlet and outlet of the reactor at 265° C. Every one hour after the start of the reaction, a sample of the resultant reaction mixture in the reactor was withdrawn, and analyzed by GC. The results of the analysis of the samples of the reaction mixture by GC showed that the conversion of cyclohexanol was 71.2%, and the selectivity for cyclohexanone was 97.3%. The analysis by GC was conducted in substantially the same manner as in the case of the amination of cyclohexanol in the above-mentioned step 3) in Example 1.

The reaction mixture was subjected to distillation to obtain a cyclohexanone product having a purity of 99%.

3) Step of Subjecting Cyclohexanone to Oximation to Obtain Cyclohexanone Oxime 68.1 g of a 37% by weight aqueous solution of hydroxylamine sulfate (which solution had been separately produced using ammonia) was charged into a stirring vessel having an inner volume of 200 ml, which was made of glass. 14.7 g of the cyclohexanone obtained in the above-mentioned step 2) and an aqueous ammonia were simultaneously charged into the stirring vessel to effect a reaction for 30 minutes while maintaining the temperature of the stirring vessel at 90° C., wherein the amount of the aqueous ammonia was adjusted so that the pH of the resultant reaction mixture became 5 to 7. The reaction mixture was analyzed by GC. The results of the analysis of the reaction mixture by GC showed that the conversion of cyclohexanone was 95.7%, and the selectivity for cyclohexanone oxime was 99.3%. The analysis by GC was conducted in substantially the same manner as in the case of the amination of cyclohexanol in the above-mentioned step 3) in Example 1.

The reaction mixture was allowed to stand still, and the oil phase of the reaction mixture was collected to thereby separate by-products, such as ammonium sulfate. The resultant, by-products-separated oil phase, was subjected to distillation to remove compounds remaining unreacted, such as cyclohexanone, thereby obtaining a cyclohexanone oxime product having a purity of 99.5% or more.

In the method employed in Comparative Example 1 for producing cyclohexanone oxime from benzene, the number of the reaction steps (which include the step of hydrogenation of benzene and the step of producing hydroxylamine) was five. The selectivity for cyclohexanone oxime was calculated by the formula described in Example 1, and found to be 73.2%. Further, since useful compounds other than cyclohexanone oxime were not detected in the reaction mixture, the total carbon yield (i.e., total yield with respect to the useful compounds) was also found to be 73.2% (in the calculation of the total carbon yield, the selectivity for cyclohexane in the hydrogenation reaction of benzene was assumed to be 100% because it is well-known that the selectivity for cyclohexane in the hydrogenation reaction of benzene is very high).

The finally obtained cyclohexanone oxime contained undesired impurities (such as butyl cyclohexyl ether, n-pentylcyclohexane, cyclohexyl acetate and hexahydrobenzaldehyde) which cause a lowering of the quality of ε-caprolactam produced from the cyclohexanone oxime, wherein each of the concentration of these undesired compounds was approximately the same as in the case of the purified cyclohexanone obtained in the above-mentioned step 1).

INDUSTRIAL APPLICABILITY

By the method of the present invention, cyclohexanone oxime, which is a useful compound as an intermediate of ε-caprolactam (ε-caprolactam is well-known as a raw material for producing nylon 6 or the like), can be produced with ease and high efficiency. Specifically, in the method of the present invention, the by-product(s) formed in the amination reaction step and/or the by-product(s) formed in the subsequent partial oxidation reaction step are/is recycled to a reaction system of the amination reaction and, then, converted to cyclohexylamine, thereby realizing a remarkable improvement in the selectivity for cyclohexanone oxime as a desired product. Especially, when the method of the present invention is practiced using, as a starting material, cyclohexanol produced by a method in which benzene is subjected to partial hydrogenation to obtain cyclohexene, and the obtained cyclohexene is subjected to hydration to obtain cyclohexanol, and/or cyclohexanone produced by subjecting the thus obtained cyclohexanol to dehydrogenation, cyclohexanone oxime can be produced with high selectivity, and with other various great advantages in that production of cyclohexanone oxime can be performed, using a simple apparatus, by a simple operation with less consumption of hydrogen, and with no need for use of a difficult reagent, such as a hydroxylamine salt. In the conventional methods for producing cyclohexanone oxime, it is usually required to use a hydroxylamine salt; however, a hydroxylamine salt can be obtained only by a method involving complicated steps, leading to disadvantages. Further, the method of the present invention is free from problems accompanying the prior art, such as generation of a by-product which is difficult to separate and which adversely affects the quality of ε-caprolactam produced from cyclohexanone oxime, and/or generation of a by-product (e.g., ammonium sulfate) which is of little commercial value. Furthermore, most of the by-products produced in the method of the present invention are recyclable, and with respect to the other by-products, which are not recyclable, most of them are useful compounds, such as cyclohexane and the like, so that generation of wastes can be suppressed to an extremely low level. Thus, the method of the present invention is commercially very advantageous.

The invention claimed is:

1. A method for producing cyclohexanone oxime, which comprises the steps of:
   (1) subjecting to an amination reaction a starting material selected from the group consisting of cyclohexanol, cyclohexanone and a mixture thereof, thereby obtaining cyclohexylamine,
   wherein said cyclohexanol is produced by a process comprising (i) subjecting benzene to partial hydrogenation to obtain a cyclohexene, and (ii) subjecting the obtained cyclohexene to hydration, and
   wherein said cyclohexanone is produced by a process comprising (i) subjecting benzene to partial hydrogenation to obtain cyclohexene, (ii) subjecting the obtained cyclohexene to hydration to obtain cyclohexanol, and (iii) subjecting the obtained cyclohexanol to dehydrogenation, and
   (2) subjecting the obtained cyclohexylamine to a partial oxidation reaction in the presence of molecular oxygen as an oxidizing agent, thereby obtaining cyclohexanone oxime,
   wherein at least one by-product selected from the group consisting of a by-product (α) formed in said step (1) and a by-product (β) formed in said step (2) is recycled to a reaction system of the amination reaction in said step (1).

2. The method according to claim 1, wherein:
   when cyclohexanol is used as the starting material in said step (1), said by-product (α) comprises at least one compound selected from the group consisting of cyclohexanone, N-(cyclohexylidene)-cyclohexylamine, dicyclohexylamine, cyclohexylaniline and aniline,
   when cyclohexanone is used as the starting material in said step (1), said by-product (α) comprises at least one compound selected from the group consisting of cyclohexanol, N-(cyclohexylidene)-cyclohexylamine, dicyclohexylamine, cyclohexylaniline and aniline, and
   when a mixture of cyclohexanol and cyclohexanone is used as the starting material in said step (1), said by-product (α) comprises at least one compound selected from the group consisting of cyclohexanol, cyclohexanone, N-(cyclohexylidene)cyclohexylamine, dicyclohexylamine, cyclohexylaniline and aniline; and
   wherein said by-product (β) comprises at least one compound selected from the group consisting of cyclohexanone, nitrocyclohexane, N-(cyclohexylidene)-cyclohexylamine and dicyclohexylamine.

3. The method according to claim 1, wherein the amination reaction in said step (1) is performed in the presence of an amination catalyst comprising at least one element selected from the group consisting of iron, cobalt, nickel, ruthenium, rhodium, palladium, iridium, platinum, chromium, copper, silver, zinc and aluminum.

4. The method according to claim 3, wherein the amination reaction in said step (1) is performed in the presence of molecular hydrogen.

5. The method according to claim 1, wherein said partial hydrogenation of benzene in step (1) is performed in the presence of a hydrogenation catalyst comprising at least one element selected from the group consisting of elements belonging to Groups 8, 9 and 10 of the Periodic Table, and water.

6. The method according to claim 1, wherein said partial hydrogenation of benzene is performed in a neutral or acidic liquid phase in the presence of (a) a hydrogenation catalyst which comprises metallic ruthenium having an average crystallite size of 200 Å or less and optionally a zinc compound, (b) water, and (c) at least one compound selected from the group consisting of an oxide of zirconium or hafnium, a water-soluble zinc compound and solid, basic zinc sulfate, wherein said hydrogenation catalyst is used in a non-supported form.

7. The method according to claim 1, wherein said hydration of cyclohexene is performed in the presence of a zeolite as a hydration catalyst.

8. The method according to claim 7, wherein said zeolite is selected from the group consisting of zeolites of ZSM-5 family.

9. The method according to claim 1, wherein the partial oxidation of cyclohexylamine in said step (2) is performed in the presence of an oxidation catalyst comprising at least one element selected from the group consisting of Ti, Zr, Hf, W, Si and Al.

* * * * *